United States Patent [19]
Twersky et al.

[11] 4,445,788
[45] May 1, 1984

[54] SOIL PROBE AND METHOD OF OBTAINING MOISTURE, TEMPERATURE AND ROOT DISTRIBUTION OF A SOIL PROFILE

[75] Inventors: Marvin Twersky; William E. Splinter; Bruce C. Sandhorst, all of Lincoln, Nebr.

[73] Assignee: The Board of Regents of the University of Nebraska, Lincoln, Nebr.

[21] Appl. No.: 373,447

[22] Filed: Apr. 30, 1982

[51] Int. Cl.³ ............................................. G01K 11/12
[52] U.S. Cl. .................................... 374/142; 73/73; 73/432 R; 374/110; 374/136; 374/155; 374/161
[58] Field of Search ............... 73/73, 432 Z; 374/136, 374/137, 142, 161, 162, 110, 155

[56] References Cited

U.S. PATENT DOCUMENTS

| | | | |
|---|---|---|---|
| 2,793,527 | 5/1957 | Turner et al. | 73/73 |
| 4,215,576 | 8/1980 | Quick et al. | 374/161 |
| 4,221,962 | 9/1980 | Black et al. | 73/73 |

FOREIGN PATENT DOCUMENTS 2931860  2/1981  Fed. Rep. of Germany ...... 374/110

*Primary Examiner*—S. Clement Swisher
*Attorney, Agent, or Firm*—Vincent L. Carney

[57] ABSTRACT

To provide a profile of simultaneous moisture, temperature and root density characteristics at different depths of soil, a soil probe is inserted in the soil with a viewing and camera section extending above the soil. Similarly, the probe provides a profile of simultaneous moisture, temperature and presence of molds, insects or other foreign matter in grain or similar media including liquid as well as solid granulated material. The portion of the probe that is in the soil or other media includes a source of light or light conveyance and windows which transmit an image of the soil at various depths along the length of the probe through light conductors for further transmission to the viewing and camera section. Liquid crystals sense the temperature of the soil at different locations and light conductors transmit color changes of the liquid crystals to the surface so that a profile may be compiled of moisture, temperature and root patterns by observation of the transmitted images in the viewing section. Viewed and photographic images can be compared with known color calibration standards to ascertain in situ moisture and temperature conditions of the soil profile.

25 Claims, 7 Drawing Figures

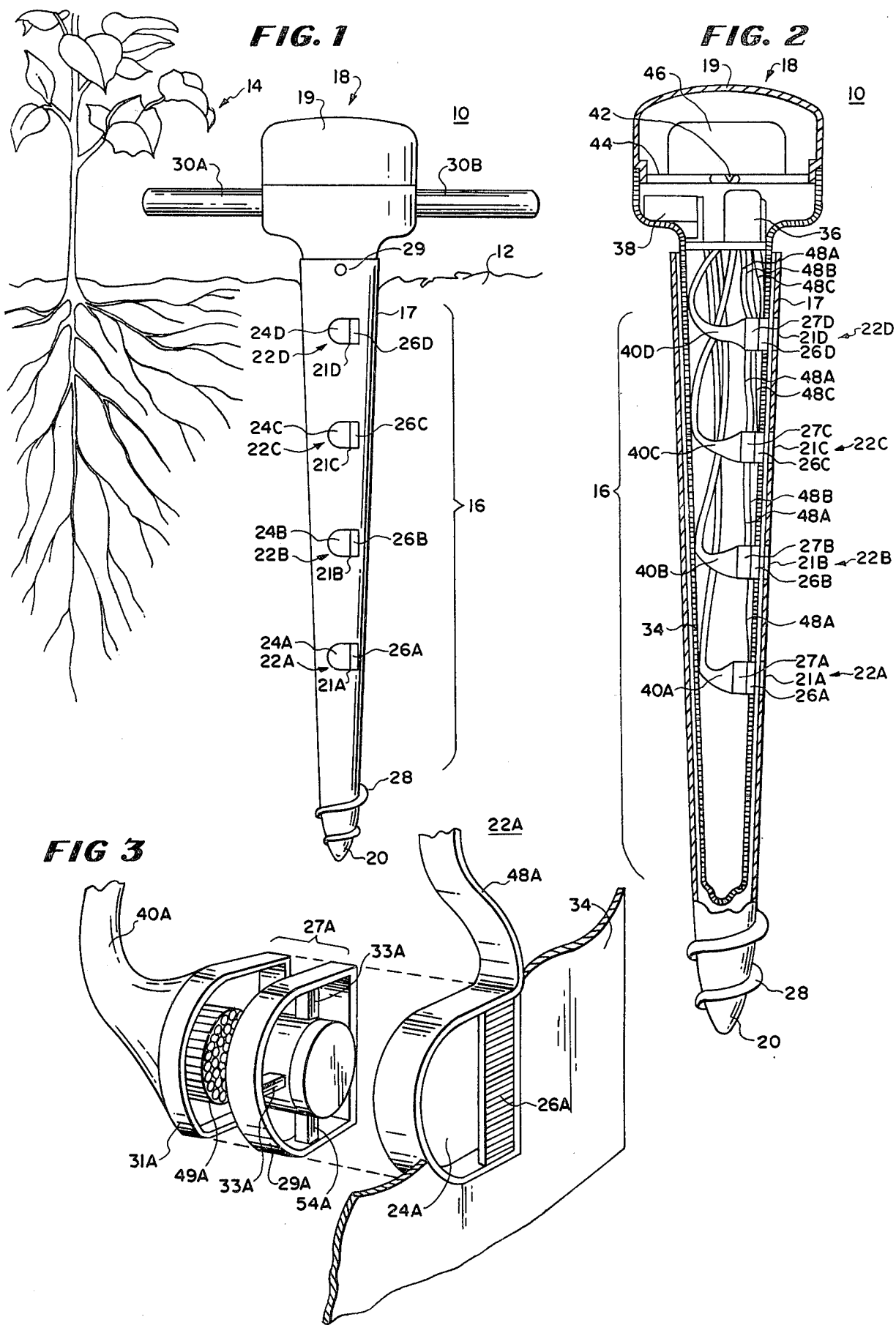

SOIL PROBE AND METHOD OF OBTAINING MOISTURE, TEMPERATURE AND ROOT DISTRIBUTION OF A SOIL PROFILE

This invention relates to instruments for measuring characteristics of a soil or granular or liquid media profile.

It has been known to measure soil and grain temperature with a thermometer or thermocouple and to measure the moisture of soil or grain with a moisture measuring apparatus. It has also been suggested to use fiber-optic devices to examine root density and patterns.

In the prior art techniques, the moisture detecting apparatus, root examination apparatus and temperature measuring apparatus are each separate instruments so that one of the temperature, moisture and root structure is measured at a given point at a time and the others later. It has been known to take cores of soil or grain for measurements or to dig trenches as well and in these techniques more than one parameter has been detected at the same time.

The prior art techniques have had the disadvantages of requiring several instruments or being relatively time consuming to use and, under some circumstances, being disruptive of the soil profile and destructive of grain samples. Moreover, the multiple instruments have often been expensive.

Accordingly, it is an object of the invention to provide a novel measuring probe.

It is a further object of the invention to provide a method and apparatus for obtaining the characteristics of soil in the form of a profile.

It is a still further object of the invention to provide a method and apparatus for conveniently measuring the parameters of soil or a granular or liquid mass.

It is a still further object of the invention to provide a portable instrument for measuring soil or grain moisture, temperature and root or mold growth or presence of insects or other foreign matter.

It is a still further object of the invention to provide an instrument for conveniently recording the characteristics of soil or grain in a profile.

In accordance with the above and further objects of the invention, a probe is provided which may be inserted in the ground or media to sense several parameters at different depths. The sensed information is transmitted to the surface where it may be viewed and, if desired, recorded.

Advantageously, the probe includes a hollow section having sensors spaced along its length to transmit information through wave guides to the surface for viewig or recording or both. In the preferred embodiment, the sensors are optical devices for forming an image of: (1) root patterns, mold growth or insects; (2) the color of the soil or media, which color indicates moisture; and (3) the color of cholesteric liquid crystals, which indicate temperature by color.

The images are transmitted to the surface by an optical system, where they may be recorded by any convenient device such as a camera. The recording may be: (1) one or more composite images, each resulting from conditions at several different depths; or (2) a sequence of individual images, each indicating a separate condition at a different depth. The colors of the soil and the colors of the liquid crystals can be calibrated for moisture content and soil temperature respectively by convenient comparison techniques. The photographic data are compared in situ with color standards such as Munsell color charts or ceramic color standards. Moreover, a permanent internal gray photographic standard may be photographed with the data to detect and to adjust for differences in photographic methods and field condition usage.

As can be understood from the above description, the probe of this invention has the advantages of simplicity, economy, ability to measure several in situ parameters at the same time, portability and ease of use.

The above noted and other features of the invention will be better understood from the following detailed description when considered in connection with the accompanying drawings, in which:

FIG. 1 is an elevational view, partly broken away and simplified, of an embodiment of the invention;

FIG. 2 is a simplified sectional view of the embodiment of FIG. 1;

FIG. 3 is a simplified, enlarged, fragmentary, perspective view of a portion of the embodiment of FIG. 1;

Figure 4:
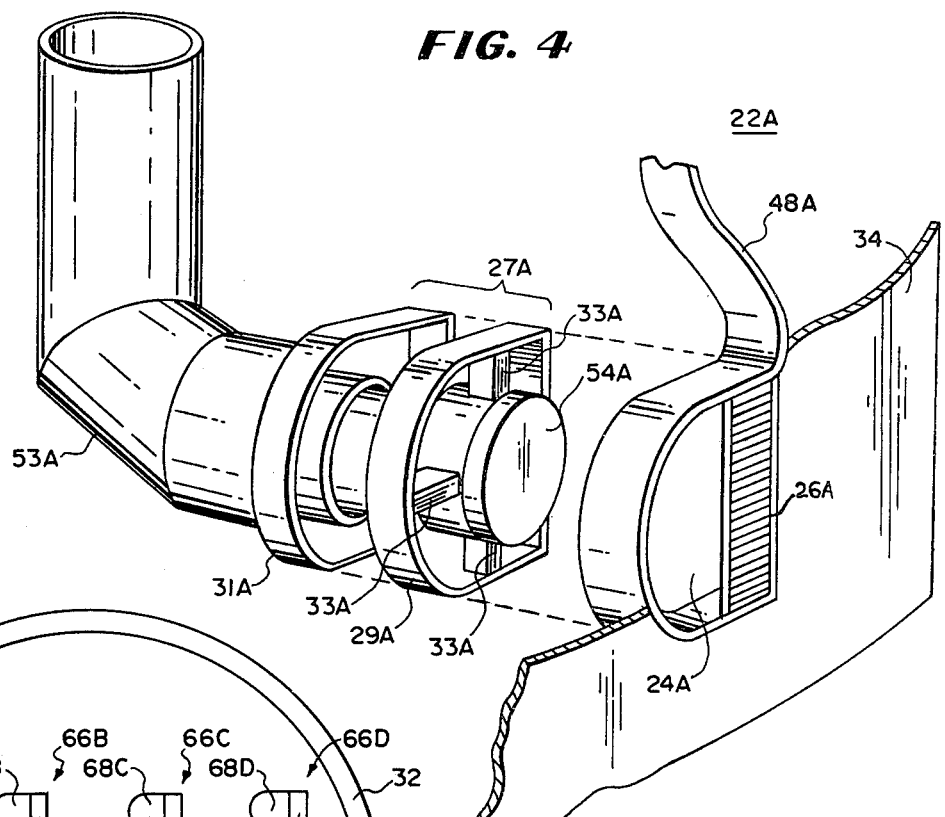
FIG. 4 is an enlarged fragmentary, perspective view of another embodiment of the portion of FIG. 3.

In FIG. 1 there is shown a profile probe 10 in place within soil or grain 12 for determining a profile of the moisture and temperature of soil or grain and the root patterns of crops 14 in that soil or presence of molds or insects in granular media. The profile probe 10 includes a profile-sensing section 16 and a viewing-and-recording section 18, fastened together. The profile-sensing section 16 is inserted in the soil or other media 12 and the separable viewing-and-recording section 18 remains above the surface 12 for viewing and recording the temperature and moisture profile and root or mold patterns as sensed by the profile-sensing section 16.

The profile-sensing section 16 generally has the shape of a hollow elongated member, which in the preferred embodiment is tapered slightly at the end 20. The profile-sensing section 16 is adapted to have its end 20 inserted first into the soil and then forced fully into the ground by turning and pushing downwardly or may be inserted fully into a preformed hole formed by devices such as soil sampling probes. The probe may be inserted directly into the granular media.

Along the length of the profile-sensing section 16 are a plurality of sets of sensing stations, four of which are shown as 22A-22D with 22A being the lowest station, 22B the next lowest and so on up to the highest station 22D. At the top and largest diameter cross-section of the profile-sensing section 16 is the separable viewing-and-recording section 18 covered by a cap 19 that attaches to and protects section 18.

The profile-sensing section 16 is covered by a protective sheath 17 having at each sensing station a corresponding one of the viewing ports 21A-21D. Beneath the sheath 17, each of the sensing stations 22A-22D includes: (1) a corresponding aperture 24A-24D approximately one-half by one-half inches in size; and (2) a corresponding one of the liquid crystals 26A-26D. The viewing ports 21A-21D permit sensing of the root structure, presence of mold or insects, color of the soil or granular media and color of the liquid crystals 26A-26D which sensed information is transmitted to the viewing-and-recording section 18 above the soil 12. Thus, the soil profile and root structure or granular media as sensed by the profile-sensing section 16 may be simultaneously viewed or recorded.

The protective sheath 17 can be adjusted in position so that it covers the apertures 24A-24D and liquid crystals 26A-26D or exposes them to the viewing ports 21A-21D as shown in FIG. 1.

To permit this adjustment in the emboodiment of FIG. 1, a spring latch 29 is mounted near the top of the protective sheath 17 and includes a pin which may be inserted in either of two circumferentially spaced apertures (not shown in FIG. 1) to hold the sheath 17 in either of two rotated positions about its longitudinal axis. In one position the sheath 17 covers the apertures 24A-24D and liquid crystals 26A-26D to protect them during insertion of the probe into the soil or granular media and in another the viewing ports 21A-21D are aligned with the apertures 24A-24D and liquid crystals 26A-26D as shown in FIG. 1 to permit viewing of the soil or granular media 12.

While four sensing stations 22A-22D are shown in FIG. 1, any appropriate number may be used. Moreover, they may not be on the same side of the profile-sensing section 16 but may be in any radial position around the profile-sensing section 16. Th profile-sensing section 16 may be of a hard plastic or metal or the like and may be of different sizes in accordance with its use. For example, a four-foot length is appropriate for many studies of soil profiles; a six-foot length is appropriate for studies of grain profiles. To facilitate its insertion in the soil or granular media, a helical thread 28 may be added to a portion or all of the profile-sensing section 16.

The seperable viewing-and-recording section 18 is coupled to the profile-sensing section 16 at the top and includes two handles shown at 30A and 30B for forcing the profile-sensing section 16 into the soil or granular media 12. The cap 19 of the viewing-and-recording section 18 is removable in the preferred embodiment so that a camera may be adjustably mounted within it to photograph areas which indicate the temperature profile, the moisture profile and the root structure or presence of mold or insects along the length of the profile-sensing section 16.

In FIG. 2 there is shown a simplified sectional view of the soil profile probe 10. As best shown in this view, the protective sheath 17 of the profile-sensing section 16 includes threads 28 extending helically along a portion or all of its length and has in it the viewing ports 21A-21D. Near the inner wall of the protective sheath 17 are: (1) a housing 34; (2) a light conductor chamber 27 connected to corresponding ones of the sensing stations 22A-22D for transmitting light to the stations and data from the stations; (3) the plurality of liquid crystals 26A-26D; and (4) a light source 36, which may include a variety of lamp and filter arrangements for selecting the desired wave length or only a lamp which emits only the appropriate frequencies of light. The lamp is powered by a battery or battery pack 38 within the separable viewing-and-recording section 18 to which it is electrically connected.

To transmit data from the sensing stations 22A-22D, the profile-sensing section 16 includes within the inner housing 34, corresponding wave guide bundles 40A-40D and corresponding wave guide bundles 48A-48D for each of the sensing stations 22A-22D.

To transmit images from the sensing stations 22A-22D, one end of each corresponding coherent wave guide bundles 40A-40D communicates with the corresponding light conductor chamber 27 and the other end extends into the coupled viewing-and-recording section 18. To transmit light to the sensing stations 22A-22D, one end of each wave guide bundles 48A-48D communicates with each sensing station and the other end is connected to the light source 36 as will be described more fully hereinafter.

An objective lens is positioned between the ends of one of the wave guides at each of the sensing stations 22A-22D and its respective aperture to receive images from outside the profile-sensing section 16 and certain temperature sensitive crystals are positioned at the end of the wave guide bundles at each of the corresponding sensing stations as will be described more fully hereinafter. Such crystals are described in U.S. Pat. No. 3,802,945.

The end 20 of the profile-sensing section 16 may be reinforced by a solid plastic section or by a metal tip or the like to facilitate penetration into the soil or granular media. The temperature sensitive crystals are of the type which change color as their temperature changes.

Within the viewing-and-recording section 18, there is mounted, in addition to the battery pack 38, a viewing face 42 and a camera 46 and/or accessories in any of a selected number of positions. While a camera 46 is contemplated in the embodiment of FIG. 2, any other type of recording apparatus may be used instead or the soil profile probe 10 may be utilized simply as a viewing probe without a recording apparatus.

Before using the profile probe 10 to view a profile of moisture, temperature, root patterns, mold, grain, insect or other foreign matter, the probe is inserted to the desired depth in the media to be studied. A scale 67 may be positioned in inverse order along its exterior length so that the depth of the probe may be determined from the scale and the sensing stations are located at predetermined locations so that, from the position of the top of the media with respect to the side of the profile-sensing section 16, the depth of each sensing station is determined.

When the profile probe 10 is in place, the light wave guide bundles 48A-48D in the profile-sensing section 16 transmit the light from the light source 36 to the sensing stations 22A-22D or if ribbons are used, they are illuminated. With the light from the wave guide bundles 48A-48D of the profile-sensing section 16, the coherent wave guide bundles 40A-40D receive images of the media through the apertures 24A-24D (FIG. 1). A grid or grids to be described hereinafter may be placed within or over the apertures 24A-24D (FIG. 1) to aid in determining the density patterns of roots, molds or insects. These images are transmitted for viewing on the viewing-and-recording section 18.

The images incidate: (1) the moisture content from the soil, grain or other media color; (2) root mold or insect density; and (3) the temperature as indicated by the color of the crystals within the sensing stations 22A-22D. Photographs may be taken by the camera 46 of either of the entire viewing section or of individual sections, one by one, which provide indicia from each sensing station. Since the location of the sensing stations are known, it is possible to provide graphic profiles of temperature, moisture and root mold, insect or other patterns from the information shown in the viewing-and-recording section 18.

In FIG. 3, there is shown a simplified, enlarged, fragmentary perspective view of the sensing station 22A including the aperture 24A, the inner housing wall 34, the liquid crystals 26A, the light bundles 48A, the coherent wave guide 40A and the wave guide housing 27A. In this embodiment, the wave guide 40A comprises a coherent bundle of light conductors 49A. The coherent light conductors 49A include a plurality of light conductors such as conventional or quartz filaments closely packed together to transmit light and an image from one end to the other. The incoherent-light bundle 48A transmits light from the light source 36 (FIG. 2) to illuminate the aperture 24A and liquid crystals 26A.

Between one end of the coherent light conductors 49A and the aperture 24A in the inner housing wall 34 are two sections 31A and 33A of housing 27A, an objective lens 54A and the light ribbon 48A mounted in the order described in aligned relationship so that light reflected onto aperture 24A and onto the liquid crystals 26A passes through the objective lens 54A and the housing 27A to the end of the bundle of image light conductors 49A. The objective lens 54A is mounted between the bundle of light conductors 49A and the aperture 24A and liquid crystals 26A by supports 33A within housing section 29A in such a position as to focus an image from the immediate opposite side of the housing 34 onto the light conductor bundler 49A for transmission to the viewing-and-recording section 18 (FIGS. 1 and 2).

In the preferred embodiment, liquid crystals 26A, having an appropriate temperature range, are permanently fixed as vertical strips on one side of the viewing apertures 24A–24D. The objective lens 54 is positioned such that the color image of the temperature sensitive liquid crystals 26A is transmitted onto the ends of some of the light conductors 49A for further transmission to the viewing-and-recording section 18 (FIGS. 1 and 2). With this construction, the temperatures sensitive color changing cell 26A assumes a color representing the temperature of the soil profile surface and this color is formed as an image on the light conductors 49A for application to the viewing-and-recording section 18 (FIGS. 1 and 2) to aid in providing a temperature profile of the soil.

The temperature sensitive color changing cell may include any suitable thermotropic liquid such as the cholestric mesomorphs described in U.S. Pat. Nos. 3,524,726 and 3,802,945 and British Pat. Nos. 1,128,590 and 1,161,039.

In the alternative, other optical systems may be used for the wave guides instead of wave guide 40A. For example, as shown in FIG. 4, the images are reflected upwardly by angularly located mirrors 53A positioned at the ends of an opaque tube 55A. The grid images 66A are transmitted to the viewing-and-recording section 18 in this embodiment through opaque-walled tube 51A instead of through fiberoptic bundles.

Figure 5:
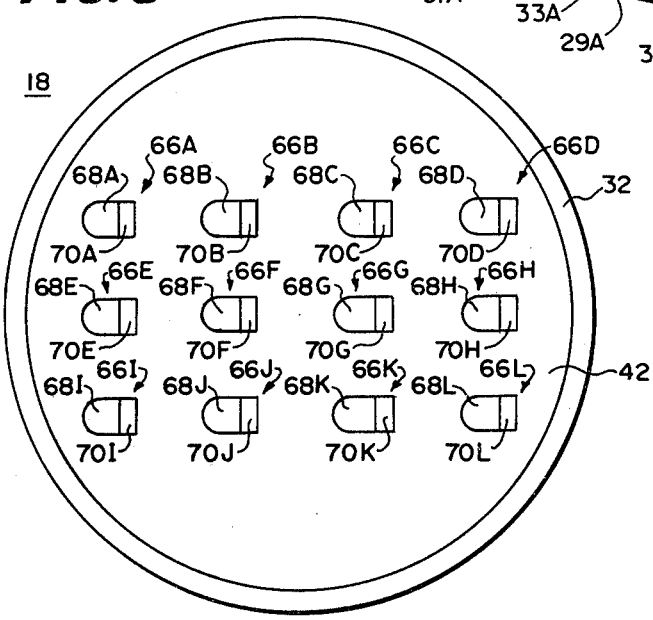
FIG. 5 is a plan view of another portion of the embodiment of FIG. 1.

In FIG. 5, there is shown a plan view of the open viewing-and-recording section 18 exposing the viewing face 42 to show a plurality of viewing stations 66A–66L, each being a composite readout of moisture, root, mold or other pattern and temperature of a viewing station. While twelve viewing stations 22A is shown in FIG. 5, this is only illustrative and more or fewer viewing stations may be used in accordance with the purpose of the soil profile probe 10 (FIG. 1).

The number of viewing stations 66A–66L corresponds to the number of sensing stations so that it represents the profile at a depth which may be determined from the depth of the sensing station. Thus, by determining the length of the probe, the position of the sensing stations along the probe and the depth to which the probe has been inserted by marks on its exterior surface, the depth represented by each of the viewing stations 66A–66L is known.

One end of each of the wave guides such as 40A illustrated for the one sensing station 22A in FIG. 3 is connected to a corresponding one of the readout stations 66A–66L with the image of the moisture and root, mold or other patterns being displayed at 68A–68L and the temperature readout being displayed at 70A–70L. With this arrangement, an image is shown in each of the readout portions 68A–68L of the media corresponding at a particular depth from which moisture content and root, mold or other growth can be determined and a readout of the temperature at that location is shown in a corresponding one of the readout portions 70A–70L.

Figure 6:
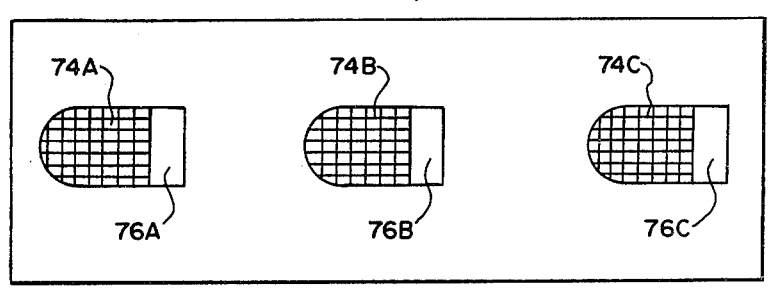
FIG. 6 is a fragmentary plan view of a portion of the embodiment of FIG. 1.

In FIG. 6, there is shown a film strip 72 having recorded upon it a plurality of images 74A–74C and 76A–76C. Each of the images 74A–74C corresponds to a photograph of the images provided at one of the moisture and root, mold or other readout portions 68A–68C and each of the images 76A–76C corresponds to the images at the temperature readout portions 70A–70C. While three pairs of images are shown in FIG. 6, it is intended that as many images be utilized as necessary to construct a proper profile.

The images are recorded in the preferred embodiment by the camera 46 (FIG. 2) which may be focused to photograph the entire viewing face 42 or individual ones of the viewing stations 66A–66D or any combination of the viewing stations desired. For that purpose the camera 46 is adjustable and able to accept accessory photographic equipment. Thus, a recording may be made which visually indicates a profile of the media which may later be used for other kinds of graphic illustrations such as charts or the like by decoding the colors indicating temperature and the color of the media which corresponds to specific calibration standards.

While a profile probe 10 has been shown which is capable of measuring visually a profile of moisture, temperature and rooting patterns, other characteristics may be determined as well or different combinations or individual ones of the moisture content, temperature and crop rooting patterns may be examined. Similarly, while the profile probe 10 has been described in connection with soil for crops, it may be used to develop a profile of other materials such as grain to determine moisture, temperature and mold growth at some depth into which it may be inserted if desired. In some such uses, sensing may be by types of radiation other than by light passing through light conductors and other types of wave guides may be desirable.

The profile probe 10 of this invention advantageously measures a characteristic of the material into which it is inserted at a plurality of points and transmits information about that characteristic to a location or to locations outside of the substance so as to be readily available for the preparation of a profile of the substance. More than one characteristic may be sensed simultaneously. Advantageously, the characteristics are sensed with the aid of light energy which is then transmitted to the location or locations for direct viewing or for recording or sensing by light sensitive instruments.

Figure 7:
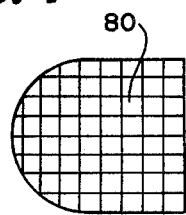
FIG. 7 is a fragmentary plan view of a portion of the embodiment of FIG. 1.

In FIG. 7 there is shown an insert 80 of transparent material shaped as one of the apertures 24A-24D (FIG. 1) or as the root on moisture sensing portions 68A-68L (FIG. 5) and having a grid superimposed upon it. The grid provides a scale of the measurement of root structure. This insert may be positioned on the apertures 24A-24D (FIG. 1) or on the sensing portions 68A-68L (FIG. 5).

From the above description, it can be understood that the profile probe 10 of this invention has several advantages such as: (1) it can make several simultaneous measurements at a single and/or several locations in the soil; (2) it is relatively inexpensive and uses parts readily available for other purposes in the market place; (3) it may conveniently be used to sense an entire profile of characteristics in the substance such as soil or similar media; and (4) it may at a single time permit viewing and recording of a profile of moisture content, root patterns, temperature and other visually indicated characteristics of soil.

Although a preferred embodiment of the invention has been described in some detail, many modifications and variations of the preferred embodiment are possible in light of the above teachings. Therefore, it is to be understood that, within the scope of the appended claims, the invention may be practiced other than as specifically described.

What is claimed is:

1. A method of determining characteristics of a substance at different locations in the substance comprising the steps of:
    inserting a probe containing a plurality of sensors on it into the substance;
    sensing a plurality of characteristics of the substance at a plurality of different locations with said sensors;
    collecting the data from said sensors at predetermined locations;
    the step of sensing said plurality of characteristics including the step of simultaneously sensing said characteristics with at least two of said sensors;
    the step of collecting data from said sensors includes the step of transmitting data from said sensors to a location outside of said substance;
    the step of sensing a plurality of characteristics further including the steps of sensing the temperature of said substance;
    sensing the moisture of the substance; and
    sensing the root growth of plant life in the substance.

2. A method according to claim 1 in which the step of sensing a characteristic of a substance includes the step of sensing a characteristic of soil.

3. A method according to claim 2 in which the step of sensing includes the step of sensing by means of electromagnetic radiation.

4. A method according to claim 3 in which the step of sensing includes the step of sensing by means of light.

5. A method according to claim 4 further including the step of carrying the probe to a site in which a characteristic of soil is to be measured.

6. A method according to claim 5 in which the step of measuring temperature includes the step of measuring temperature by placing a material, which changes color in accordance with temperature, adjacent to said substance.

7. A method according to claim 6 in which the step of collecting data includes the step of transmitting light through light conductors.

8. A method according to claim 7 in which the step of collecting data includes the step of calibrating said data against standards which are sensed by said sensors prior to sensing the characteristics of said substance.

9. A method of determining characteristics of a substance at different locations in the substance comprising the steps of:
    inserting a probe containing a plurality of sensors on it into the substance;
    sensing a plurality of characteristics of the substance at a plurality of different locations with said sensors;
    collecting the data from said sensors at predetermined locations;
    the step of sensing said plurality of characteristics including the step of simultaneously sensing said characteristics with at least two of said sensors;
    the step of collecting data from said sensors including the step of transmitting data from said sensors to a location outside of said substance;
    the step of sensing a plurality of characteristics further including the steps of sensing the temperature of said substance, sensing the moisture of the substance, sensing the root growth of plant life in the substance, sensing a characteristic of soil, sensing by means of electromagnetic radiation and sensing by means of light;
    carrying the probe to a site in which the plurality of characteristics of soil are to be measured;
    the step of measuring temperature including the step of measuring temperature by placing a material, which changes color in accordance with temperature, adjacent to said substance;
    the step of collecting data including the step of transmitting light through light conductors and the step of calibrating said data against standards which are sensed by said sensors prior to sensing the characteristics of said substance; and
    photographing said data.

10. A method of determining characteristics of a substance at different locations in the substance comprising the steps of:
    inserting a probe containing a plurality of sensors on it into the substance;
    sensing a plurality of characteristics of the substance at a plurality of different locations with said sensors;
    collecting the data from said sensors at a predetermined location;
    the step of collecting data from said sensors including the step of transmitting data from said sensors to a location outside of said substance;
    the step of sensing a plurality of characteristics including the step of sensing the temperature of said substance; and
    the step of sensing further including the step of sensing the moisture of the substance and the root growth of plant life in the substance.

11. A method according to claim 10 in which the step of sensing includes the step of sensing by means of electromagnetic radiation and by means of light.

12. A method according to claim 11 in which the step of measuring temperature includes the step of measuring temperature by placing a material, which changes color in accordance with temperature, adjacent to said substance.

13. A method of determining characteristics of a substance at different locations in the substance comprising the steps of:
   inserting a probe containing a plurality of sensors on it into the substance;
   sensing a plurality of characteristics of the substance at a plurality of different locations with said sensors;
   collecting the data from said sensors at a predetermined location; and
   the step of sensing a plurality of characteristics including the step of sensing the temperature of said substance, the moisture of the substance, the root growth of plant life in the substance and a characteristic of soil.

14. A method according to claim 13 in which the steps of sensing includes the step of sensing by:
   means of light;
   placing a material which changes color in accordance with temperature adjacent to said substance; and
   transmitting light through light conductors.

15. A method according to claim 14 in which the step of collecting data includes the step of calibrating said data against standards which are sensed by said sensors prior to sensing the characteristics of said substance.

16. A method according to claim 15 further including the step of photographing said data.

17. A method of determining characteristics of a substance at different locations in the substance comprising the steps of:
   inserting a probe containing a plurality of sensors on it into the substance;
   sensing a plurality of characteristics of the substance at a plurality of different locations with said sensors;
   collecting the data from said sensors at a predetermined location;
   the step of sensing including the step of sensing by means of light;
   the step of measuring temperature including the step of measuring temperature by placing a material, which changes color in accordance with temperature, adjacent to said substance;
   the step of collecting data including the step of transmitting light through light conductors;
   the step of collecting data including the step of calibrating said data against standards which are sensed by said sensors prior to sensing the characteristics of said substance; and
   the step of photographing said data.

18. Apparatus comprising:
   a hollow shell;
   at least two means for sensing a characteristic of soil mounted to said shell;
   indicating means for indicating characteristics of said material in response to said signals from said sensing means;
   means for transmitting signals from said sensing means to said indicating means;
   at least one of said means for sensing a characteristic including a sensing means for sensing temperature; and
   said means for sensing temperature including liquid crystals and means for obtaining a signal representing color of said liquid crystals.

19. Apparatus according to claim 18 in which said means for transmitting includes a means for transmitting images of said characteristics of soil.

20. Apparatus according to claim 19 further including a source of electromagnetic radiation within said shell.

21. Apparatus according to claim 20 in which said electromagnetic radiation is within the frequency spectrum of light and said means for transmitting includes light conductors.

22. Apparatus according to claim 21 further including a means adapted to mount a camera.

23. Apparatus comprising:
   a hollow shell;
   at least two means for sensing a characteristic of soil mounted to said shell;
   indicating means for indicating characteristics of said material in response to said signals from said sensing means;
   means for transmitting signals from said sensing means to said indicating means; and
   said means for sensing temperature including liquid crystals and means for obtaining a signal representing color of said liquid crystals.

24. Apparatus according to claim 23 in which said means for transmitting includes a means for transmitting images of said characteristics of soil; and
   said electromagnetic radiation is within the frequency spectrum of light and said means for transmitting includes light conductors.

25. Apparatus according to claim 24 further including a means adapted to mount a camera.

* * * * *